(12) United States Patent
Beale et al.

(10) Patent No.: US 8,968,420 B2
(45) Date of Patent: Mar. 3, 2015

(54) SURGICAL PROSTHETIC DEVICE CUTTING TOOL

(75) Inventors: Jeff Beale, Bartlett, TN (US); Harold Taylor, Memphis, TN (US); Jeffrey R. Chapin, Jamaica Plain, MA (US); Jared Alden Judson, Topsfield, MA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1616 days.

(21) Appl. No.: 12/104,648

(22) Filed: Apr. 17, 2008

(65) Prior Publication Data

US 2009/0264887 A1 Oct. 22, 2009

(51) Int. Cl.
- A61B 17/00 (2006.01)
- B26B 17/00 (2006.01)
- A61F 2/68 (2006.01)
- A61B 17/88 (2006.01)
- A61B 17/29 (2006.01)

(52) U.S. Cl.
CPC ..... *A61B 17/8863* (2013.01); *A61B 2017/2934* (2013.01)
USPC ............ 623/65; 623/64; 30/180; 606/79

(58) Field of Classification Search
USPC ...................... 606/83; 30/180, 228
See application file for complete search history.

(56) References Cited

U.S. PATENT DOCUMENTS

| | | | |
|---|---|---|---|
| 2,990,613 A | 7/1961 | Keane | |
| 3,177,583 A * | 4/1965 | Fischer et al. | 30/180 |
| 3,255,525 A * | 6/1966 | Frenzel | 30/180 |
| 3,372,480 A | 3/1968 | Rozmus | |
| 3,670,411 A | 6/1972 | Peters | |
| 4,109,381 A * | 8/1978 | Pellenc | 30/228 |
| 4,707,918 A * | 11/1987 | Smith et al. | 30/228 |
| 4,760,644 A * | 8/1988 | Yirmiyahu et al. | 30/180 |
| 5,018,275 A | 5/1991 | Huang | |
| 5,134,776 A | 8/1992 | Moody | |
| 5,711,078 A | 1/1998 | Patton et al. | |
| 5,715,604 A | 2/1998 | Lanzoni | |
| 5,836,937 A | 11/1998 | Holmes | |
| 5,875,554 A * | 3/1999 | Vogelsanger | 30/228 |
| 5,901,447 A * | 5/1999 | Dunning | 30/228 |
| 5,988,027 A | 11/1999 | Lenox | |
| 6,860,888 B2 | 3/2005 | Ball et al. | |
| 7,165,439 B2 | 1/2007 | Lefavour et al. | |

OTHER PUBLICATIONS

International Searching Authority, Invitation to Pay Additional Fees and Where Applicable, Protest Fee, Jul. 14, 2009.

* cited by examiner

*Primary Examiner* — Bruce E Snow
*Assistant Examiner* — Melissa Hoban
(74) *Attorney, Agent, or Firm* — Sorell, Lenna & Schmidt, LLP

(57) ABSTRACT

A surgical tool includes a drive assembly including a head assembly and a cutting assembly coupled to the drive assembly. The cutting assembly includes a first blade having a first cutting surface and a first contact surface. The cutting assembly also includes a second blade pivotally coupled to the first blade. The second blade has a second cutting surface and a second contact surface. The first and second contact surfaces define a constant travel ratio.

14 Claims, 9 Drawing Sheets

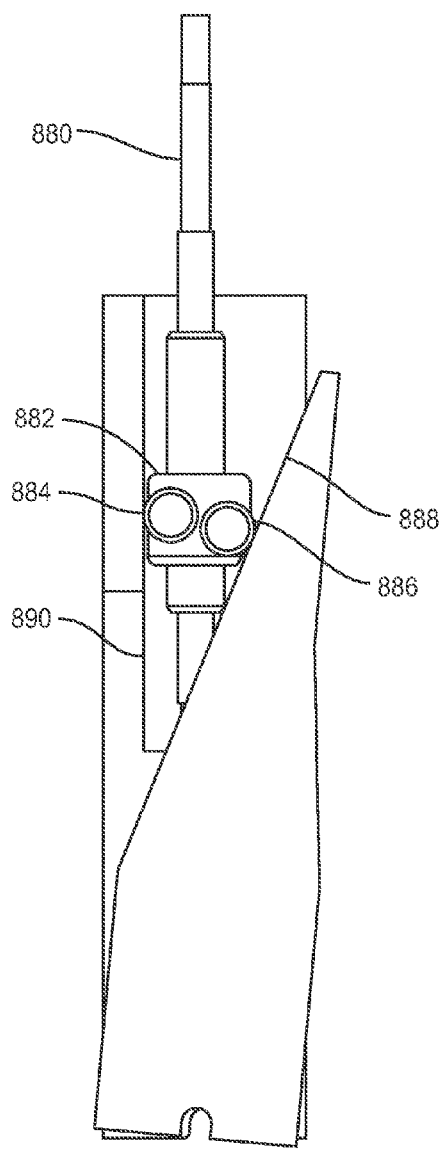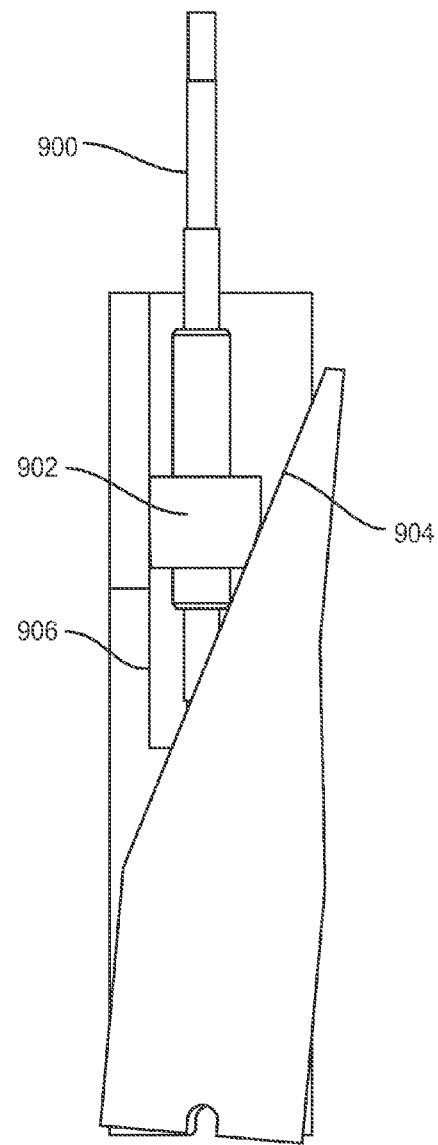
*FIG. 8*  *FIG. 9*

SURGICAL PROSTHETIC DEVICE CUTTING TOOL

BACKGROUND

1. Field of the Disclosure

This disclosure, in general, relates to cutting tools for use in surgical applications and in particular, cutting tools for augmenting surgically implanted medical devices.

2. Description of the Related Art

Increasingly, surgeons are turning to implantable prosthetic devices to repair hard tissue damage or to correct defects in skeletal features. For example, implantable prosthetic devices have been used to repair broken bones in the arms and legs or to repair broken features associated with joints. In addition, implantable prosthetic devices have been used to treat degenerative defects in the spine or to correct spinal curvature.

In particular, when such implantable prosthetic devices are used in high stress environments, the materials used are able to withstand the forces exerted by movement of the body. For example, implantable prosthetic devices used to repair bones within the legs generally are able to withstand compressive and torsional forces associated with walking, running or jumping. Similarly, implantable prosthetic devices used in relation to the spine, are able to withstand the compression and torsional forces associated with body motion. As such, surgeons typically turn to structural material such as metals, including titanium. Such metals are advantageously strong, but are disadvantageously difficult to adapt during surgery. For example, titanium is difficult cut and shape in the operating room.

When implanting implantable prosthetic devices, it is typical for a surgeon to adjust the dimensions of the prosthetic device to suit a particular patient. For example, when fixing vertebrae relative to each other, a physician may implant prosthetic device, mechanically coupling it to the vertebrae. During surgery, the surgeon may cut the rod to a desired length once the dimensions are determined during surgery. Often, such reshaping or sizing of material is performed iteratively outside of the body. For example, a physician or a surgeon makes a first measurement of the skeletal feature and cuts the prosthetic device to the approximate dimensions of the skeletal feature. The physician then compares in vivo the size of the prosthetic device relative to the skeletal features and again removes the implantable prosthetic device to make adjustments ex vivo. Such a process is time consuming in an environment where time is critical, such as during surgery.

As such, an improved tool and method of preparing an implantable prosthetic device would be desirable.

BRIEF DESCRIPTION OF THE DRAWINGS

The present disclosure may be better understood, and its numerous features and advantages made apparent to those skilled in the art by referencing the accompanying drawings.

FIG. 8 and FIG. 9 include illustrations of a head assembly.

The use of the same reference symbols in different drawings indicates similar or identical items.

DESCRIPTION OF THE EMBODIMENTS

In accordance with embodiments herein, a tool for use during surgery is disclosed that enables in-situ swaging, crimping, crushing, or cutting of implants within a patient. As described in more detail herein, the tool includes a motor contained within a housing and connected to the housing, an effector coupled to the motor and configured to move in a translational direction to exert a force on an implant. In accordance with an aspect, the tool further includes a reaction arm coupled to the housing and the implant, the reaction arm configured react to the force applied to the implant by the effector. As used herein, cutting refers generally include compression of an implant material, such as a rod or plate and generally includes swedging, crimping, cutting, or crushing. It will be noted, that particular designs, especially of the blades, that are more suitable for crushing or cutting.

In certain embodiments, the tool includes an assembly, such as a cutting assembly that is operably coupleable to the housing. In one particular embodiment, the cutting assembly includes the reaction arm that is coupled to the housing and configured to engage an implant. In a more particular embodiment, the cutting assembly includes cutting blades and one of the cutting blades can be the reaction arm. In accordance with other certain embodiments, the reaction arm is a blade that is fixed and stationary with respect to the position of the effector, such that only the other blade moves with respect to translational movement of the effector.

In another particular embodiment, a cutting tool useful in surgical applications includes a cutting assembly coupled to a drive assembly. The drive assembly includes a head assembly that advances to manipulate the cutting assembly. In particular, the drive assembly is sealed in a manner to render the drive assembly sterilizable by autoclaving. In addition, the cutting assembly is sterilizable by autoclaving.

In an exemplary embodiment, the nature of the cutting tool permits cutting of implants in proximity to a surgical site within a patient and, in particular, may be used within the surgical site after the prosthetic device is implanted. For example, a prosthetic device may be at least partially implanted within a patient. A surgeon may then shape portions of the prosthetic device in proximity to the surgical site or even within the surgical site.

Figure 1:
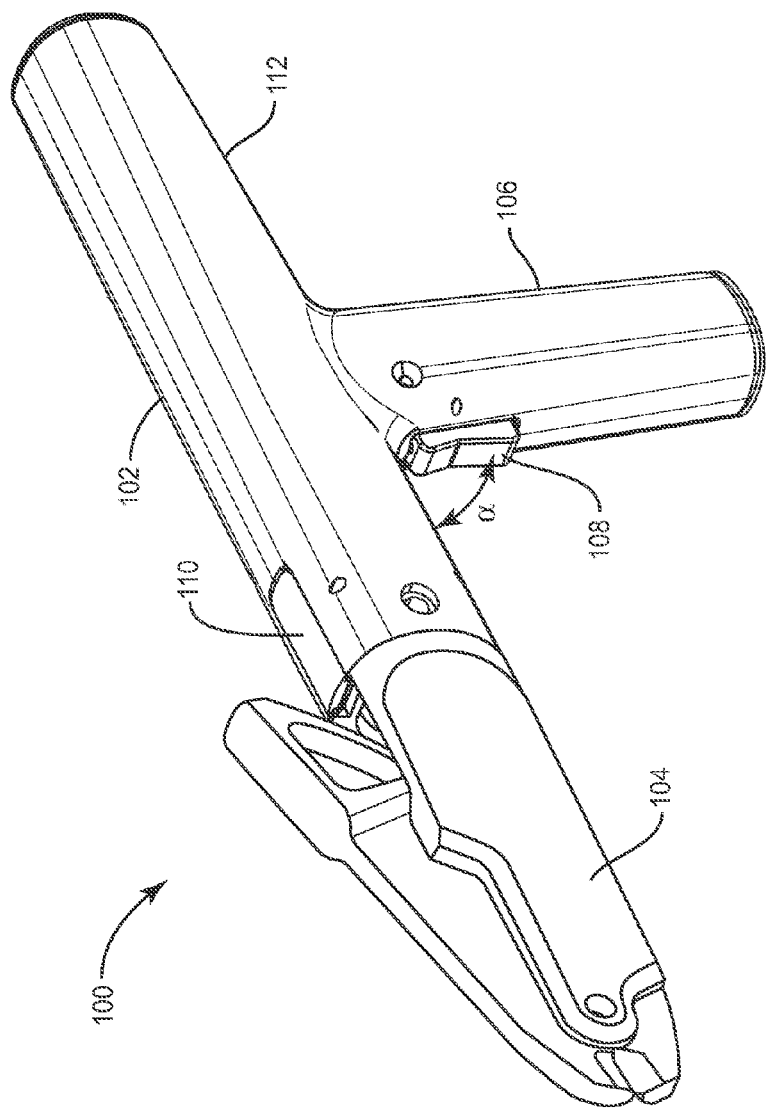
FIG. 1 and FIG. 2 include isometric drawings of a surgical cutting tool.
Figure 2:
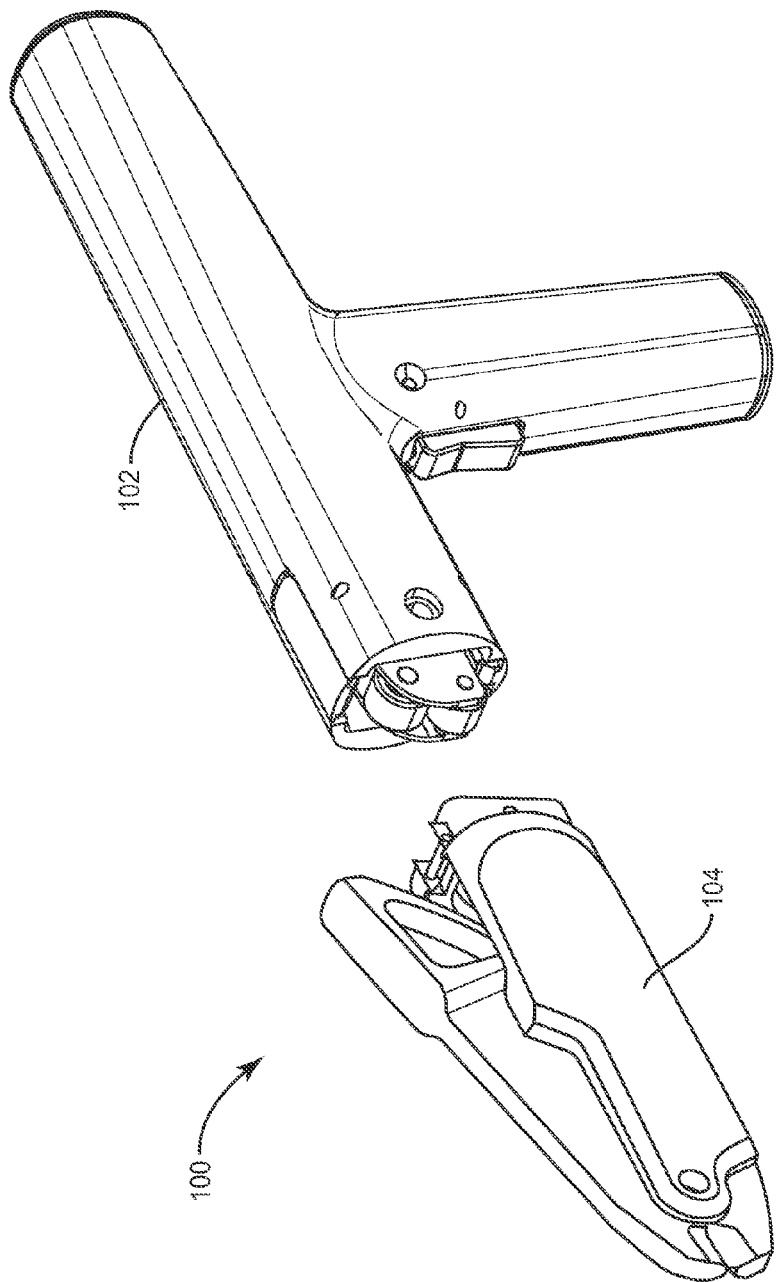

FIG. 1 and FIG. 2 include illustrations of an exemplary embodiment of a cutting tool. The cutting tool 100 may include a drive assembly 102 and a cutting assembly 104. As illustrated in FIG. 1, the drive assembly 102 may be coupled to the cutting assembly 104. For example, the drive assembly 102 may be coupled to the cutting assembly 104 using a quick connect coupling, such as a clip mechanism 110. As illustrated in FIG. 2, the drive assembly 102 and the cutting assembly 104 may be separated. In particular, the drive assembly 102 may be configured to couple to various cutting assemblies, such as cutting assembly 104. For example, a plurality of different types of cutting assemblies, each configured to implement a different cutting method, may be available for use with the drive assembly 102. In addition, the cutting assembly 104 may be replaced in the event of tool wear. Alternatively, the cutting assembly 104 may be permanently coupled to the drive assembly 102.

The drive assembly 102 may include a handle 106 coupled to a body 112. Relative to the body 112, the handle 106 may be positioned closer to a cutting end than to the back end of the body 112. In addition, the handle 106 may have a pistol-type configuration. Further, an activating switch assembly 108 may be positioned on the handle 106.

In the embodiment illustrated in FIG. 1, the handle 106 extends perpendicularly from the body 112. Alternatively, the handle 106 may sweep forward or may sweep backward. For example, an angle a defined between the front face of the handle 106 and a longitudinal axis of the body 112 may be less than 90°, such as not greater than about 65°, not greater than about 45°, or even about 35°. Alternatively, the handle 106 may be greater than 90°, such as at least 120°.

Figure 3:
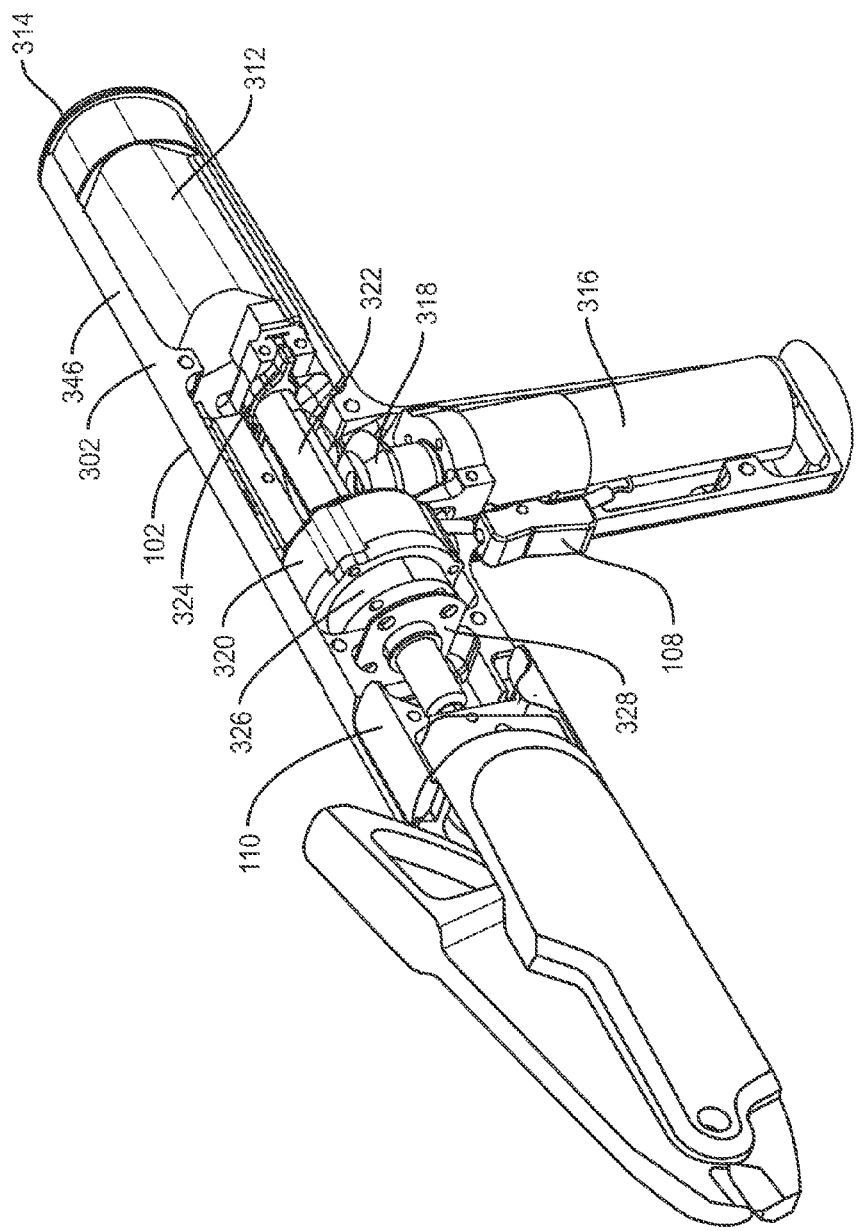
FIG. 3 includes an isometric drawing of a driver mechanism.
Figure 4:
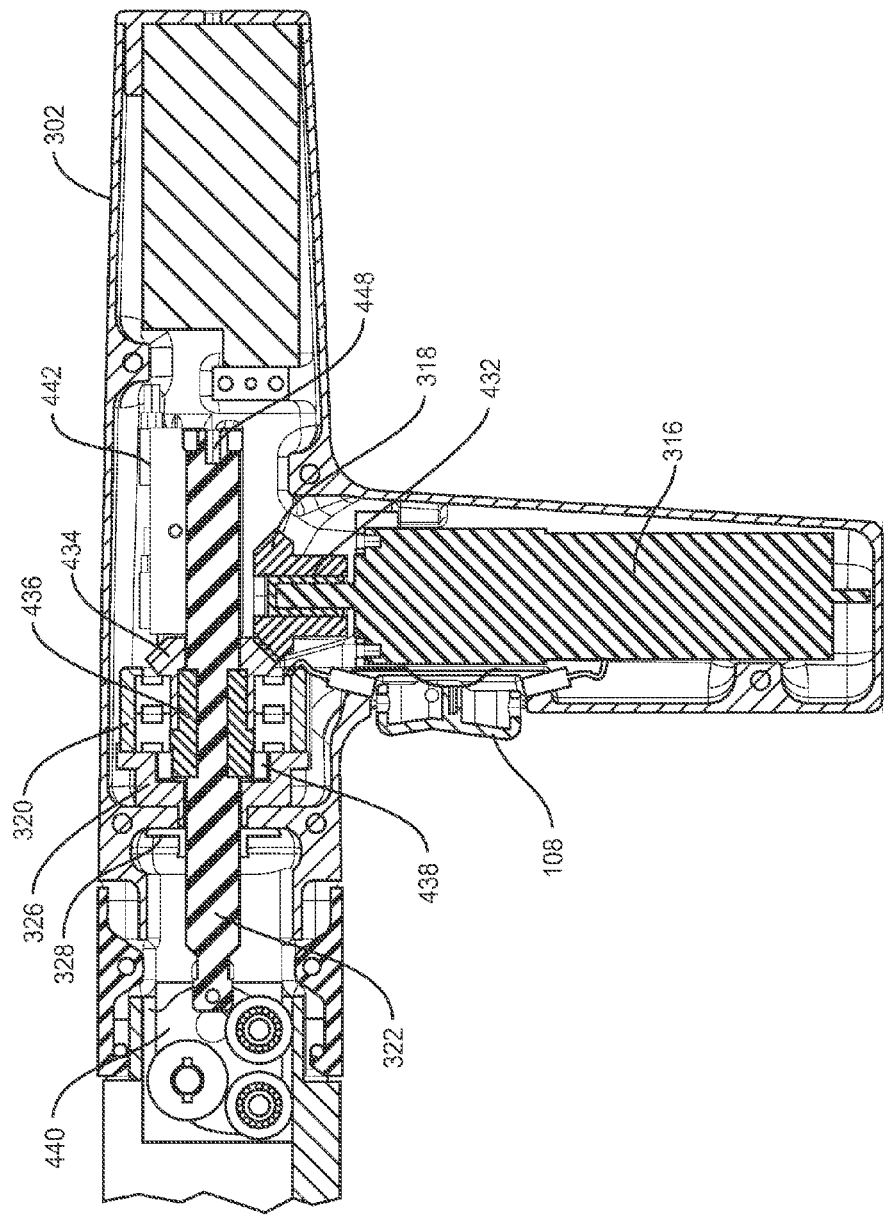
FIG. 4 includes a cut away illustration of a driver mechanism.

Turning to FIG. 3 and FIG. 4, a motor 316 manipulates an effector that includes lead screw 322 using miter gears 318 and 434 to motivate a head assembly 440 against a cutting assembly, resulting in the manipulation of one or more of the cutting blades. The mechanism is stored within a housing 302. The driving assembly may also include a power source, such as a battery 312 located at a back end 346 of the housing 302. In addition, a cap 314 is attached to the battery 312 and positioned at the back end 346 of the housing 302. The cap 314 facilitates proper placement of the battery 312 within the housing 302, and in one particular example, the cap 314 may further include a seal, to aid sealing of the back end 346 of the housing in a manner to permit autoclaving. Further, the housing 302 or the stopper 314 may include electrical access to the power source, such as the battery 312, to permit recharging. Alternatively, the battery 312 may be removable to permit battery replacement or recharging of the battery 312 externally to the housing 302.

In an embodiment, the battery 312 is electrically coupled to the motor 316. For example, the motor 316 may be a DC electric motor. As illustrated, the motor 316 is located within the handle portion of the housing 302. The motor 316 may be electrically connected to and may be activated by a switch assembly 108. In an example, the switch assembly 108 may be configured to activate the motor 316 to drive the lead screw 322 in a forward direction towards the cutting tool or assembly. Additionally, the switch assembly 108 may be configured to activate the motor 316 to operate in a reverse manner moving the lead screw 322 away from the cutting assembly.

In a particular example, the motor 316 and the lead screw 322 are secured in relative position by a chassis 320. Alternatively, the housing 302 may include features that secure the motor 316 and an assembly associated with the lead screw 322 in relative position without a chassis 320.

In operation, the motor 316 drives a lower miter gear 318. The lower miter gear 318 may be coupled to a shaft of the motor 316 having an optional gear shaft collar 432, as illustrated in FIG. 4. The lower miter gear 318 drives an upper miter gear 434. The upper miter gear 434 may manipulate a lead screw nut 436 to motivate the lead screw 322 in a direction toward the cutting assembly. Further, the motion of the motor 316, upper and lower miter gears 434 and 318, and lead screw nut 436 may be reversed to motivate the lead screw 322 in a backwards direction towards the backside 346 of the housing 302.

To secure the lead screw nut 436 in place, the drive assembly may further include a thrust nut 438 threaded to the lead screw nut 436. In addition, a thrust plate 326 may be secured to the chassis 320 and more particularly, may be used to engage a head assembly 440 for actuating a cutting assembly. As such, the lead screw nut 436 is secured in place to motivate the lead screw 322 in both forward and reverse directions.

In an example, the lead screw 322 may include an anti-rotation strut 324. As illustrated, the anti-rotation strut 324 is secured to a back end of the lead screw 322, and may be configured to move at least partially within channels 448 within the housing 302. As a result, the anti-rotation strut 324 may limit the rotational movement of the lead screw 322 as it travels forward and backward.

Furthermore, the drive assembly may include a limit switch 442 electrically coupled to the motor 316 or the battery 312. In particular, a limit switch 442 may limit operation of the motor when the lead screw 322 advances to a desired forward or aft position.

In general, the lead screw 322 is coupled to a head assembly 440. When the lead screw 322 advances, it drives the head assembly 440 in a direction towards a cutting assembly to contact surfaces of cutting blades and manipulate the blades to perform a cutting action. Similarly, when the lead screw 322 is motivated in an aft direction, the head assembly 440 is motivated away from the cutting assembly releasing any cutting force.

Figure 5:
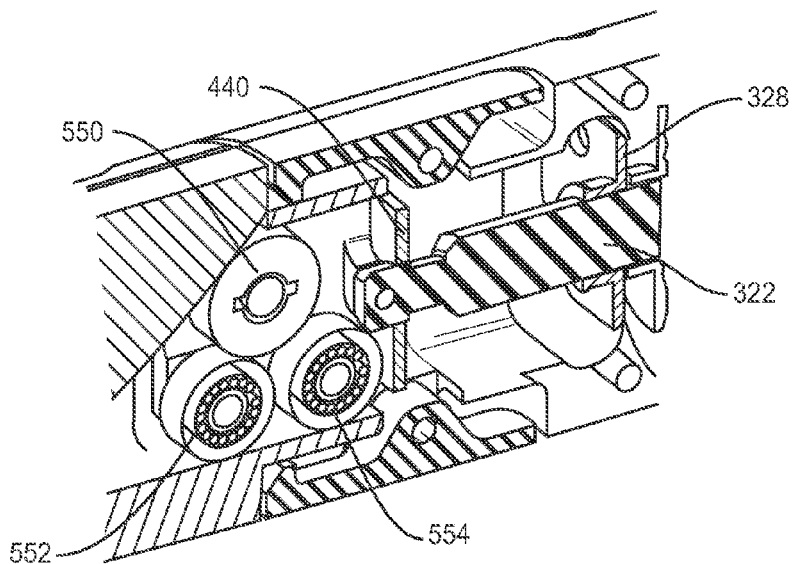
FIG. 5 includes an illustration of a head assembly.

As illustrated in more detail in FIG. 5, the lead screw 322 may be coupled to a back end of the head assembly 440. The lead screw 322 may advance and retract through a faceplate 328 (also illustrated in FIG. 3 and FIG. 4). The faceplate 328 may provide a seal around the lead screw 322, preventing fluids from contaminating the drive assembly mechanisms located within the housing 302. Likewise, one or more sealing elements can be placed rearward of the faceplate 328 to form a seal in the rear of the housing adjacent the battery pack 312, facilitating formation of a sealed portion within the housing to avoid damage to certain components, such as the motor 316. In particular, the formation of a sealed portion within the housing allows the tool to undergo high temperature sterilization of the drive assembly, such as autoclaving. In addition, the internal components, especially those described above in relation to FIG. 3 and FIG. 4, are formed of material compatible with high temperature sterilization techniques, such as autoclaving.

Figure 6:
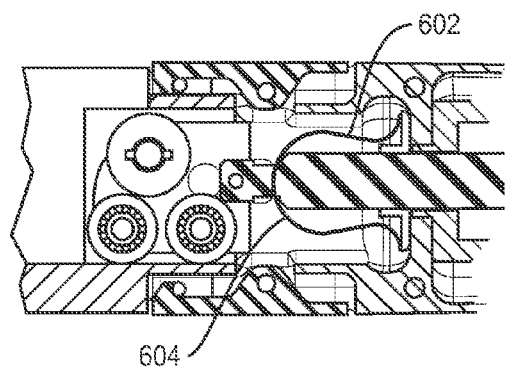
FIG. 6 and FIG. 7 include illustrations of a sealed lead screw assembly.
Figure 7:
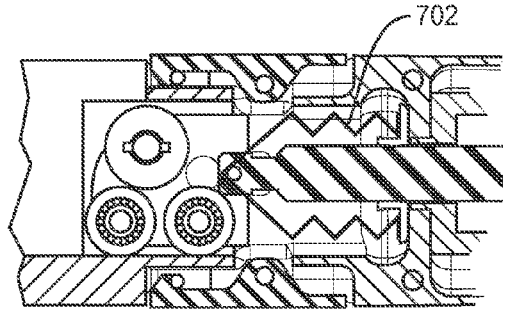

In alternative embodiments, additional seals and mechanisms to prevent fluid from entering the housing 302 may include a diaphragm or a bellows coupled to or surrounding the lead screw 322. For example, FIG. 6 includes an illustration of the lead screw 322 extending through a diaphragm 602. In an example, the diaphragm 602 is coupled to a shoulder 604 of the lead screw 322. The diaphragm 602 may be formed of an elastomeric material and may be configured to expand or contract to an extent based on the full travel range of the lead screw 322. FIG. 7 illustrates an alternative embodiment including a bellows 702, which surrounds the lead screw 322. The bellows 702 may be configured to expand or contract to accommodate the full travel range of lead screw 322. The bellows 702 may be formed of a metal, polymer, or a combination thereof. In both examples, the diaphragm 602 or the bellows 702 are sealed and secured to the housing 302 or a face plate 328 providing an additional seal and preventing liquid incursion within the housing 302.

Returning to FIG. 5, the illustrated embodiment of the head assembly 440 may include a three-wheel assembly, which may contact surfaces of blades of the cutting assembly to manipulate the motion of the blades. The wheels 550, 552, and 554 may be configured to contact surfaces of a cutting assembly and apply force to those surfaces motivating a cutting action by the cutting blades. In particular, the head assembly 440 may include upper wheel 550 that contacts a moving blade and the lower wheels 552 and 554 may contact a surface of a fixed blade. As such, travel of the head assembly 440 in a direction towards the cutting assembly results in the movement of the blades relative to one another by virtue of the forces applied by the wheels 550, 552, and 554.

In a particular embodiment, the positioning of the wheels 550, 552, and 554 is configured to balance forces to reduce torque applied to the lead screw as a result of the opposing forces of the cutting blades. For example, the wheels 550, 552, and 554 may be disposed on the head assembly 440 in a triangular configuration to balance torsional forces to substantially limit torque on the lead screw. In the illustrated embodiment, the lower wheels 552 and 554 are positioned adjacent to each other on the head assembly 440 and the upper wheel 550 is positioned behind the first of the lower wheels 552 relative to a longitudinal access of the lead screw 322.

Alternatively, the head assembly 440 may include more or fewer wheels or may include no wheels at all. In an alternative embodiment illustrated in FIG. 8, the lead screw 880 is coupled to a head assembly 882. The head assembly 882 includes a first wheel 884 that engages a surface of a fixed blade 890. In addition, the head assembly 882 includes a second wheel 886 that engages a surface of a movable blade 888. In a further embodiment illustrated in FIG. 9, the lead screw 900 is coupled to a head assembly 902 which has surfaces configured to engage and slide along the surfaces of the blades 904 and 906. In a separate embodiment, a head assembly may include one wheel or may include four or more wheels. Notably, in the alternative embodiments illustrated in FIGS. 8 and 9, the lead screw 880 and 900 may rotate to engage a head assembly 882 and 902.

Figure 10:
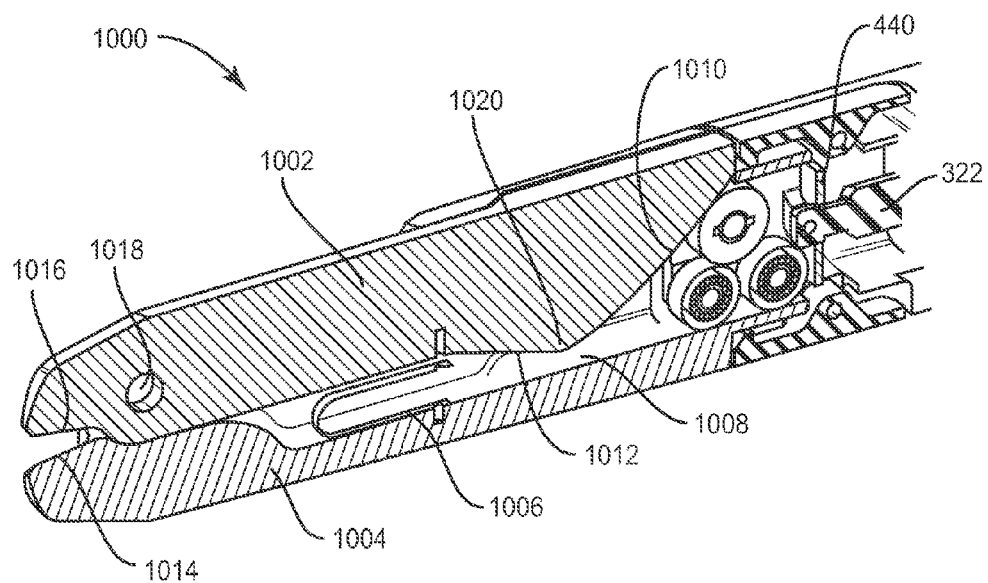
FIG. 10 includes an illustration of a cutting assembly.

Turning to the cutting assembly, FIG. 10 includes an illustration of an exemplary cutting assembly 1000. In general, the cutting assembly may be configured to cut components of a prosthetic device through actions, such as crushing, pinching, shearing, torquing, or drawing, among others. In particular, the cutting assembly 1000 may be configured to cut elongated components of a prosthetic device, such as rods, bars, tubes, or combinations thereof. For example, the components of the prosthetic may be formed of metal or metal alloys, including, for example, titanium nickel, cobalt or tungsten, or may be formed of a polymer, a ceramic, a composite material, or a combination thereof. In an example, the component may have an effective diameter in a range of about 2 mm to about 10 mm. For example, a rod may have a diameter of at least 3 mm or not greater than 10 mm. Further, the cutting assembly 1000 may be configured to provide a cutting force of at least 500 $lbs_f$, such as at least 1500 $lbs_f$. In particular, the cutting assembly 1000 may be configured to provide a cutting force in a range of about 1500 $lbs_f$ to about 5000 $lbs_f$. In addition, the cutting assembly 1000 may be configured to provide a cutting pressure of at least 100 ksi (100,000 psi), such as a cutting pressure in a range of about 500 ksi to about 1000 ksi. In the illustrated example of FIG. 10, the cutting assembly 1000 is illustrated that may pinch or crush a component of a prosthetic device.

The cutting assembly 1000 includes an upper blade 1002 and a lower blade 1004 pivotally coupled at 1018. The upper blade 1002 includes a cutting edge 1016 and the lower blade 1004 includes a cutting edge 1014. In the illustrated embodiment, lower blade 1004 is a fixed blade and the upper blade 1002 is configured to rotate relative to the fixed blade 1004 causing a pinching action near cutting surfaces 1014 and 1016, which abut each other in a closed position. Alternatively, the blades 1002 and 1004 may be configured to provide relative motion either by providing a fixed blade with a movable blade or by providing two movable blades.

In an exemplary embodiment, a head assembly 440 may travel in a direction towards the cutting end, contacting a surface 1008 of the lower blade 1004 and contacting a surface 1010 of the upper blade 1002. As a result, the blades rotate relative to each other around the pivot point 1018 causing a pinching action between cutting edges 1014 and 1016. Optionally, the driver mechanism may permit withdrawal of the head assembly 440, motivating travel of the driver 440 in a direction away from the cutting assembly. As a result, a pinching force applied between the cutting surfaces 1014 and 1016 may be diminished.

In a further example, the cutting assembly 1000 may include a return spring 1006 that motivates the blades into an open position when the head assembly 440 is withdrawn. Alternatively, the return spring 1006 may provide enough force to drive the head assembly 440 in a reverse direction when the drive mechanisms, such as the motor, are not activated.

In a particular embodiment, the relative surfaces of the blades 1002 and 1004 that contact the head assembly 440 may be configured to provide rotational movement causing a cutting action in response to a forward movement of the head assembly 440. Herein, the rotational movement initiating a cutting action is designated as a positive rotational direction whereas rotational movement to withdraw a cutting force is designated as a negative rotational direction. In addition, travel of the head assembly 440 in a direction towards the cutting assembly 1000 is designated as a positive traveling direction and travel of the head assembly 440 in the direction opposite the cutting assembly 1000 is designated as a negative travel direction. The relationship of head assembly travel relative to the rotational movement of the cutting assembly may thus be characterized by a ratio of the rotational movement to the travel of the head assembly. For example, if the positive travel of the head assembly results in a rotation of the cutting blades in a positive direction relative to one another, a travel ratio is positive. On the other hand, if travel of the head assembly in a positive direction results in a rotation of the blades relative to each other in a negative direction or results in no rotation of the blades relative to each other, the travel ratio is non-positive and may be negative.

In a particular embodiment, the contact surfaces of the blades 1002 and 1004 may be configured to provide a positive travel ratio. For example, a lower fixed blade 1004 may include a flat surface 1008 and the upper blade 1002 may include a curved surface 1010, which contacts the head assembly 440. The relative configurations of the contact surface 1008 and the contact surface 1010 may be configured to provide a positive travel ratio. In a particular example, the relative shape of the surfaces 1008 and 1010 may be configured to provide a constant travel ratio.

In a further exemplary embodiment, the contact surfaces of the blades 1002 and 1004 may be configured in two sections. For example, a first section may provide a positive travel ratio while a second section may provide a non-positive travel ratio. For example, the upper blade 1002 may include two contact surfaces 1010 and 1012. As above, the contact surface 1010 relative to the contact surface 1008 may provide a positive travel ratio when the head assembly 440 contacts the relative surfaces 1008 and 1010. As the head assembly is driven forward, this positive travel ratio manipulates the cutting surfaces 1014 and 1016 closer to one another. In a particular example, the positive travel ratio resulting from a shape of the surfaces 1008 and 1010 may be constant.

When the travel of the head assembly 440 reaches an apex or transition point 1020, the surface 1010 ends and the surface 1012 begins. As a result, the travel ratio may shift. The resulting travel ratio is derived from the relative shape of surfaces 1012 and 1008. In a particular example, a ratio resulting from the shape of the relative surfaces 1008 and 1012 is non-positive, such as zero. As a result, when a head assembly 440 is in contact with surfaces 1012 and 1008, the cutting surfaces 1014 and 1016 may not move relative to each other with continued travel of the head assembly 440 in a positive direction. Alternatively, the relative surfaces 1008 and 1012 may provide a negative travel ratio resulting in a separating of cutting surfaces 1014 and 1016 in response to continued advancement of the head assembly in a positive direction.

In a particular embodiment, the apex 1020 and the surface 1012 may correspond to a closed position of the cutting surfaces 1014 and 1016. For example, the cutting surfaces 1014 and 1016 may be in contact with each other when the head assembly 440 is in contact with the apex 1020 and the surface 1012 may be parallel to the surface 1008 as the head assembly 440 travels forward. In particular, such a design may prevent over-travel of the cutting surfaces 1014 and 1016, reducing blade wear and damage.

Still, in accordance with another embodiment, the transition from a positive travel ratio or a non-positive travel ratio can be controlled electronically. For example, when the travel of the head assembly 440 reaches a certain point, corresponding to the apex or transition point 1020 described above, an electronic switch can disengage the motor 316 from the lead screw 322, thus stopping the translational movement of the head assembly 440. As a result, the travel ratio may be controlled electronically, resulting in a change from a positive travel ratio before a certain point and engagement of an electronic switch, to a non-positive travel ratio after the head assembly 440 has traveled a particular translational distance and engaged an electronic switch. After engaging such an electronic switch, the travel ratio may be changed again to a negative travel ratio resulting in reversing the direction of the head assembly 440 and a separating of cutting surfaces 1014 and 1016. This may be accomplished by use of an integrated circuit or logic programmed to drive the motor in reverse after the electronic switch has been triggered.

Figure 11:
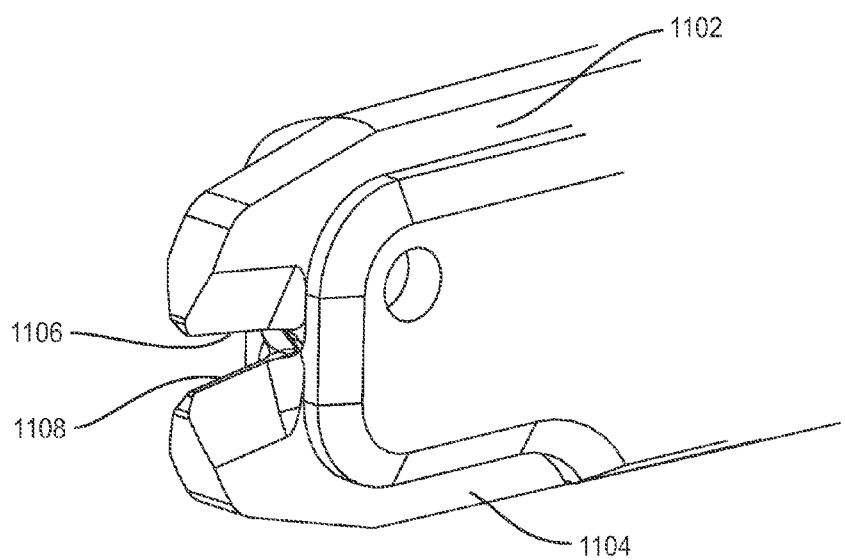
FIG. 11 includes an illustration of interchangeable blade tips.

In addition, cutting surfaces may be formed of removable components. For example, as illustrated in FIG. 11, upper and lower cutting blades 1102 and 1104 may include exchangeable cutting surfaces 1106 and 1108. For example, the exchangeable cutting surfaces 1106 and 1108 may be removably coupled to the blades 1102 and 1104, permitting exchange of dull blades or cutting surfaces for sharp cutting surfaces. Alternatively, the cutting surfaces 1106 and 1108 may be exchanged based on the materials being used in the implantable prosthetic devices. For example, titanium prosthetic devices may utilize stronger cutting surfaces, which are typically more expensive, while ceramic or plastic implantable prosthetic devices may utilize cutting surfaces of differing material that, owing to their particular material properties, may utilize cutting surfaces of differing shape or hardness. In an example, a plurality of exchangeable cutting components may be provided or may be available.

Figure 12:
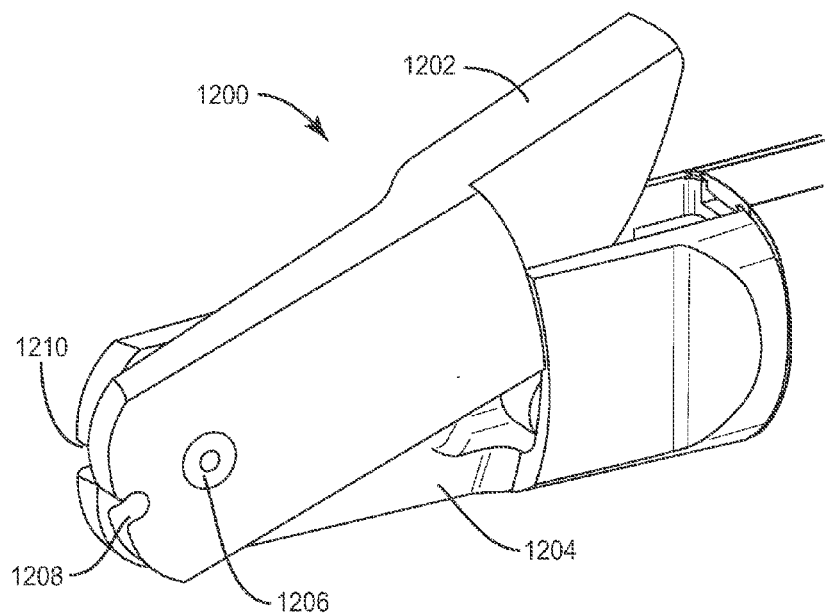
FIG. 12, FIG. 13, FIG. 14, and FIG. 15 include illustrations of exemplary cutting assemblies.
Figure 13:
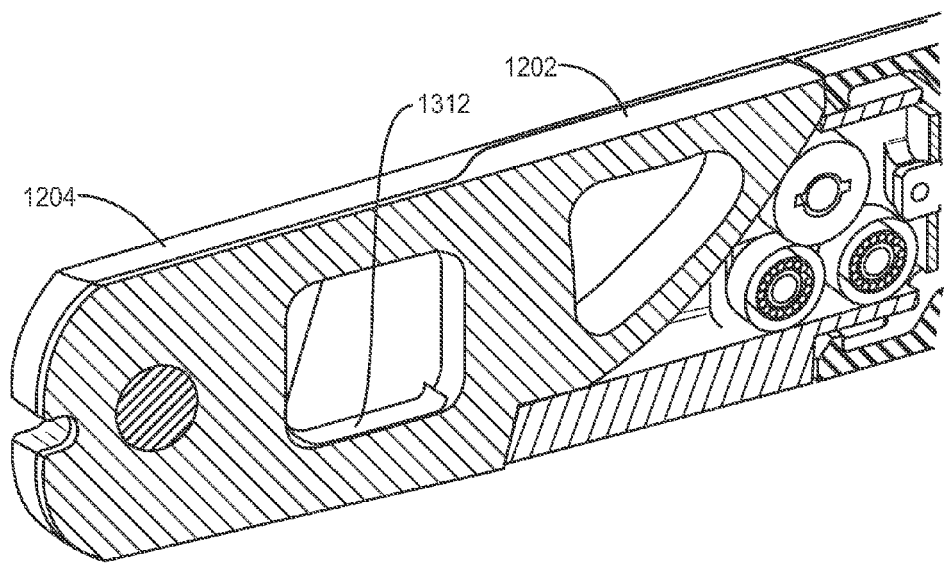

While the cutting assembly 1000 illustrated in FIG. 10 includes a crushing or pinching cutting surface, other cutting mechanisms may be provided that shear. FIG. 12 and FIG. 13, for example, include illustrations of an embodiment of a shearing mechanism. As illustrated in FIG. 12, the cutting assembly 1200 includes a cutting blade 1202 and a cutting blade 1204, which pivot relative to each other around a pivot point 1206 and slideably engage curvilinearly to provide a shearing motion.

In an example, the blade 1202 may include a receiving notch 1208 and the blade 1204 may include a receiving notch 1210. When the receiving notches 1208 and 1210 are aligned with each other, a component of an implantable prosthetic device may be inserted through the receiving notches 1208 and 1210. Travel of a head assembly may result in the motion of the blade 1202 relative to the blade 1204 causing the receiving notches 1208 and 1210 to move out of alignment. The resulting movement of the receiving notches 1208 and 1210 results in a shearing action, cutting the component of the implantable prosthetic device. Furthermore, as illustrated in FIG. 13, the blades for cutting assembly may include a return spring 1312 to return the blades 1202 and 1204 into an aligned position when the head assembly travels in a reverse direction.

Figure 14:
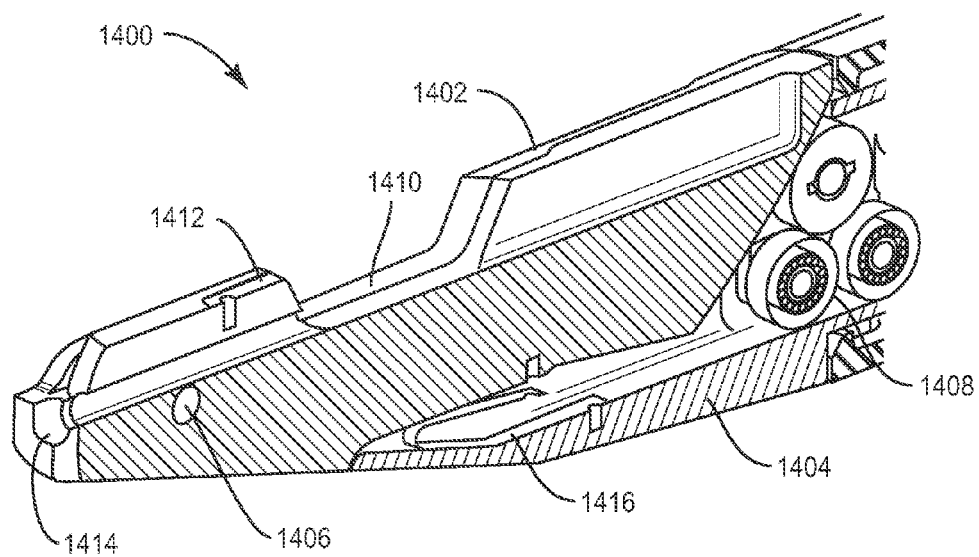
Figure 15:
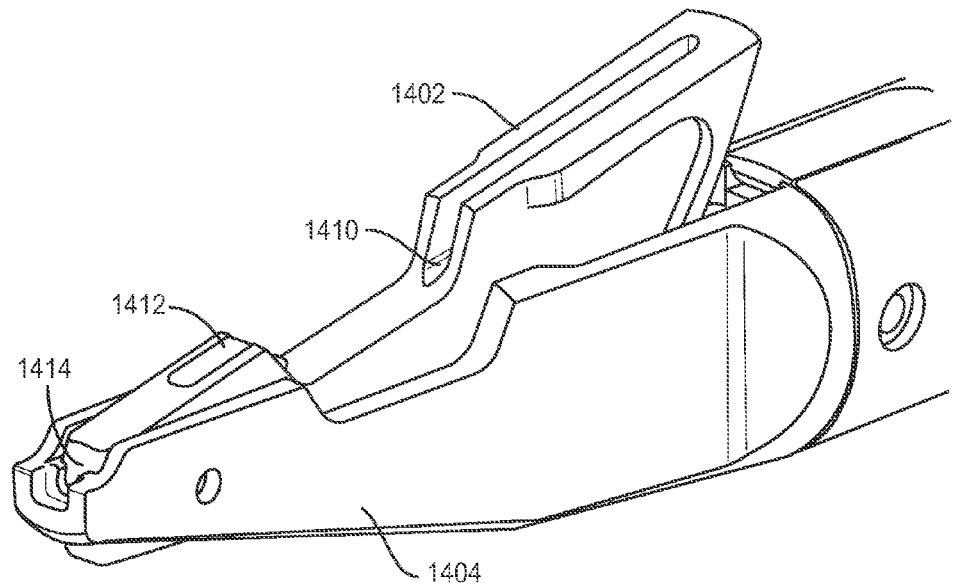

In a further embodiment illustrated in FIG. 14 and FIG. 15, a post cutter embodiment of a cutting assembly is provided. For example, blade 1402 and blade 1404 are positioned relative to each other. In particular, the blade 1402 is received within a recess of the blade 1404 and is positioned within or is surrounded by blade 1404 and coupled to the blade 1404 at a pivot point 1406. When aligned with an axis of the channel 1410, as illustrated in FIG. 14, a receiving surface 1414 of blade 1404 is slideably engaged with a channel 1410 of the blade 1402. In a particular example, the receiving surface 1414 may be semicircular and the channel 1410 may be circular. Alternatively, the receiving surface 1414 and the channel 1410 may be configured to receive components having a cross-section, such as a circular cross-section, a triangular cross-section, a hexagonal cross-section, a square or rectangular cross-section, another polygonal cross-section, or any combination thereof.

A component of an implantable prosthetic device, such as a rod, tube or post, may be inserted through the receiving surface 1414 and into the channel 1410. When a head assembly 1408, such as a drive nut, is motivated in a positive forward direction, the blades 1402 and 1404 move relative to each other to move the receiving surface 1414 out of alignment with the channel 1410, shearing the component of the implantable prosthetic device.

In addition, the blade 1402 may include a retention spring 1412. The retention spring 1412 may secure separated portions of the component of the implantable prosthetic device that are sheared from the rest of the component.

In a particular embodiment, the drive assembly and the cutting assembly may be useful during surgical procedures, particularly those involving implantable prosthetic devices. For example, the drive assembly may be sterilized, such as through autoclaving, and the cutting assembly may be sterilized, such as through autoclaving. The drive assembly and the cutting assembly may be separate or may be coupled during autoclaving. In particular, the drive assembly and cutting assembly are coupled in preparation for surgery or during surgery.

The assembled cutting tool may then be used to cut a portion of an implantable prosthetic device. For example, the portion of the prosthetic device may be at least partially implanted within a patient. The cutting tool may be used to cut the portion of the prosthetic device after implanting. In a particular example, the portion may extend from a surgical site on a patient. In another example, the cutting tool and, in particular, the cutting assembly may be configured to fit within the surgical site and cut the portion in vivo.

In a particular example, a surgical tool includes a drive assembly including a head assembly and a cutting assembly coupled to the drive assembly. The cutting assembly includes a first blade having a first cutting surface and a first contact surface. The cutting assembly also includes a second blade pivotally coupled to the first blade. The second blade has a second cutting surface and a second contact surface. The first and second contact surfaces define a constant travel ratio.

In another exemplary embodiment, a surgical tool includes a drive assembly including a head assembly. The surgical tool also includes a cutting assembly coupled to the drive assembly. The cutting assembly includes a first blade having a first cutting surface and a first contact surface. The first contact surface has a first portion and a second portion. The cutting assembly also includes a second blade pivotally coupled to the first blade. The second blade has a second cutting surface and a second contact surface. The first portion of the first contact surface and the second contact surface define a positive travel ratio. The second portion of the first contact surface and the second contact surface define a non-positive travel ratio.

In a further exemplary embodiment, a surgical tool includes a drive assembly including a lead screw coupled to a head assembly. The head assembly includes at least two wheels. The surgical tool also includes a cutting assembly coupled to the drive assembly. The cutting assembly includes a first blade having a first cutting surface and a first contact surface. The cutting assembly also includes a second blade pivotally coupled to the first blade. The second blade has a second cutting surface and a second contact surface. A first wheel of the at least two wheels contacts the first contact surface and a second wheel of the at least two wheels contacts the second surface. The at least two wheels are positioned on the head assembly to substantially limit torque on the lead screw.

In an additional exemplary embodiment, a surgical tool includes a drive assembly including a lead screw coupled to a head assembly. The head assembly includes three wheels. The surgical tool also includes a cutting assembly coupled to the drive assembly. The cutting assembly includes first and second blades. The first blade has a first cutting surface and a first contact surface. The second blade is pivotally coupled to the first blade. The second blade has a second cutting surface and a second contact surface. A first wheel of the three wheels contacts the first contact surface and a second wheel and a third wheel of the three wheels contacts the second surface. The three wheels are positioned on the head assembly to substantially limit torque on the lead screw.

In another exemplary embodiment, a surgical tool includes a housing including a sealed portion, an electric motor disposed within the sealed portion of the housing, a drive mechanism mechanically coupled to the motor and at least partially disposed within the sealed portion of the housing, and a head assembly extendable from the housing. The surgical tool is autoclavable.

In a further exemplary embodiment, a tool for use during surgery includes a housing having a proximal end and a distal end opposite the proximal end, a motor disposed within the housing, a power source connected to the motor, and a cutting end connected to the housing and configured to sever a portion of an implantable prosthetic device.

In an additional exemplary embodiment, a tool for use during surgery includes an autoclavable housing including a sealed portion containing a motor. The tool also includes a cutting end connected to the housing including autoclavable components. The cutting end comprises a first cutting arm and a second cutting arm pivotally connected to the first cutting arm. At least one of the first cutting arm and second cutting arm are configured to move relative to the other cutting arm and sever a portion of an implant.

In another exemplary embodiment, a tool for in vivo cutting of an implanted rod during a surgical process includes a housing, a motor disposed within the housing, a power source electrically connected to the motor, and a cutting end connected to the housing and mechanically coupled to the motor. The cutting end is configured to apply a force sufficient to sever a component of an implanted prosthetic device. The implanted prosthetic device disposed within a patient when the force is applied.

In a further exemplary embodiment, a method of implanting a prosthetic device includes autoclaving a drive assembly, autoclaving a cutting assembly, coupling the drive assembly to the cutting assembly, and cutting a portion of the prosthetic device.

In an additional exemplary embodiment, a method of implanting a prosthetic device includes at least partially implanting a component of a prosthetic device within a patient and cutting with a cutting tool the at least partially implanted component after at least partially implanting. The cutting tool includes an autoclavable drive assembly and an autoclavable cutting assembly.

In accordance with another aspect a tool for use during surgery is disclosed that includes a motor contained within a housing and connected to the housing, an effector coupled to the motor and configured to move in a translational direction to exert a force on an implant, and a reaction arm coupled to the housing and the implant, the reaction arm configured react to the force applied to the implant by the effector. In one embodiment of this aspect the tool further includes an assembly operably coupleable to the housing and configured to engage the effector. In one particular embodiment, the assembly includes the reaction arm. In another embodiment of this aspect, the assembly includes a first blade and a second blade, wherein the first and second blades configured to swage the implant. In still another embodiment the second blade is the reaction arm. In accordance with one particular embodiment, the first blade is coupled to the effector and is configured to rotate in response to the movement in the translational direction by the effector and the second blade is stationery with respect to movement of the effector. Still, in another embodiment, the first blade and the second blade are configured to crimp the implant. In still another embodiment, the first blade and the second blade are configured to cut the implant.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes, " "including, " "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A surgical tool comprising:
    a drive assembly including a head assembly; and
    a cutting assembly coupled to the drive assembly, the cutting assembly including:
    a first blade having a first cutting surface and a first contact surface;
    a second blade pivotally coupled to the first blade, the second blade having a second cutting surface and a second contact surface, the first and second contact surfaces defining a constant travel ratio; and
    a return spring disposed between the first blade and the second blade configured to move the first and second blades into an open position when the head assembly is withdrawn and provides a force to drive the head assembly in a reverse direction when a drive mechanism is not activated.

2. The surgical tool of claim 1, wherein the first blade and second blade rotate relative to each other around a pivot point configured to cause a pinching action between the first blade and second blade.

3. The surgical tool of claim 1, wherein the second contact surface is substantially flat and wherein the first contact surface is curved.

4. The surgical tool of claim 1, wherein the first blade includes a third contact surface, the third contact surface and the second contact surface defining a non-positive travel ratio.

5. The surgical tool of claim 4, wherein the non-positive travel ratio is zero.

6. The surgical tool of claim 4, wherein an apex defined between the first contact surface and the third contact surface of the first blade corresponds to a closed blade position, the first and second cutting surfaces in contact in the closed blade position.

7. The surgical tool of claim 1, wherein the first and second cutting surfaces slideably engage when the first and second blades move to a closed position.

8. The surgical tool of claim 1, further comprising a handle having a pistol-like configuration.

9. A surgical tool comprising:
    a drive assembly including a head assembly; and
    a cutting assembly coupled to the drive assembly, the cutting assembly including:
    a first blade having a first cutting surface and a first contact surface, the first contact surface having a first portion and a second portion;
    a second blade pivotally coupled to the first blade, the second blade having a second cutting surface and a second contact surface, the first portion of the first contact surface and the second contact surface defining a positive travel ratio, the second portion of the first contact surface and the second contact surface defining a non-positive travel ratio; and
    a return spring disposed between the first blade and the second blade that motivates the first and second blades into an open position when the head assembly is withdrawn and provides a force to drive the head assembly in a reverse direction when a drive mechanism is not activated.

10. The surgical tool of claim 9, wherein the positive travel ratio is constant.

11. The surgical tool of claim 9, wherein the second blade has a fixed position relative to the drive assembly and wherein the first blade rotates relative to the second blade.

12. A tool for use during surgery comprising:
    an electric motor contained within a housing and connected to the housing;
    an effector coupled to the motor and configured to move in a translational direction to exert a force on an implant;
    a reaction arm coupled to the housing and the implant, the reaction arm configured to counterbalance the force applied to the implant by the effector; and
    a return spring disposed with the reaction arm configured to move the reaction arm into an open position when the effector is withdrawn and provides a force to drive the head assembly in a reverse direction when the motor is not activated.

13. The tool of claim 12, wherein the tool further comprises an assembly operably coupleable to the housing and configured to engage the effector.

14. The tool of claim 13, wherein the assembly comprises the reaction arm.

* * * * *